United States Patent
Jones et al.

(10) Patent No.: US 7,034,931 B2
(45) Date of Patent: Apr. 25, 2006

(54) METHOD TO GRAIN INSPECT DIRECTIONALLY SOLIDIFIED CASTINGS

(75) Inventors: Howard B. Jones, Glastonbury, CT (US); John H. Bluege, Lake Park, FL (US)

(73) Assignee: United Technologies Corporation, Hartford, CT (US)

(*) Notice: Subject to any disclaimer, the term of this patent is extended or adjusted under 35 U.S.C. 154(b) by 316 days.

(21) Appl. No.: 10/610,982

(22) Filed: Jun. 30, 2003

(65) Prior Publication Data

US 2004/0263832 A1   Dec. 30, 2004

(51) Int. Cl.
G01N 21/00 (2006.01)

(52) U.S. Cl. .................................. 356/237.2

(58) Field of Classification Search ............ 356/237.2, 356/237.3, 445, 446, 30, 31

See application file for complete search history.

(56) References Cited

U.S. PATENT DOCUMENTS

| | | | |
|---|---|---|---|
| 5,149,978 A | 9/1992 | Opsal et al. | |
| 5,426,506 A | 6/1995 | Ellingson et al. | |
| 5,589,690 A | 12/1996 | Siewert et al. | |
| 6,005,913 A | 12/1999 | Zombo et al. | |
| 6,285,449 B1 | 9/2001 | Ellingson et al. | |
| 6,580,502 B1 * | 6/2003 | Kuwabara | 356/237.3 |
| 6,812,047 B1 * | 11/2004 | Borden et al. | 356/369 |
| 2004/0036862 A1 * | 2/2004 | Liang et al. | 356/237.2 |
| 2004/0042001 A1 * | 3/2004 | Vaez-Iravani et al. | 356/237.2 |

* cited by examiner

*Primary Examiner*—Layla G. Lauchman
*Assistant Examiner*—Juan D. Valentin, II
(74) *Attorney, Agent, or Firm*—Bachman & LaPointe, P.C.

(57) ABSTRACT

A method for detecting defects in metallic parts, comprising the steps of providing a metallic surface comprising a repeating microstructure and at least one surface defect, redirecting an incident light beam off of an area of the metallic surface comprising the at least one surface defect thereby forming a redirected light beam, observing the redirected light beam, detecting at least a portion of the redirected light beam resulting from redirection off of the at least one surface defect.

26 Claims, 4 Drawing Sheets

METHOD TO GRAIN INSPECT DIRECTIONALLY SOLIDIFIED CASTINGS

BACKGROUND OF THE INVENTION (1) Field of the Invention

The present invention relates to method, and apparatus for so performing, to evaluate grain defects in directionally solidified nickel base alloy castings. More specifically, the present invention relates to an inspection method to optically discriminate amongst features such as grain defects in directionally solidified nickel base alloy castings or other materials with at least partially coherent light scattering properties.

(2) Description of Related Art

Many methods exist for identifying grain defects in metallic parts. Such methods are often time consuming and expensive.

What is needed is a fast and economical method for evaluating grain defects, particularly grain defects present in directionally solidified nickel base alloy castings.

SUMMARY OF THE INVENTION

Accordingly, it is an object of the present invention to provide an inspection method to evaluate grain defects in directionally solidified nickel base alloy castings or other materials with at least partially coherent light scattering properties.

In accordance with the present invention, a method for detecting defects in metallic parts comprises the steps of providing a metallic surface comprising a repeating microstructure and at least one surface defect, redirecting an incident light beam off of an area of the metallic surface comprising the at least one surface defect thereby forming a redirected light beam, observing the redirected light beam, detecting at least a portion of the redirected light beam resulting from redirection off of the at least one surface defect.

DETAILED DESCRIPTION OF THE PREFERRED EMBODIMENT(S)

The present invention discloses an inspection method whereby grain defects may be detected and evaluated in directionally solidified metal castings or other materials with at least partially coherent light scattering properties. As such, the method of the present invention broadly encompasses any and all metallic components possessing a discernable grain structure. Such metallic components include, but are not limited to, compressor blades, compressor vanes, turbine blades, and turbine vanes, particularly those composed of nickel based alloys. Note that the use of the term "coherent" does not imply the requirement for the use of coherent light. It simply means that the materials have the ability to generate a diffraction grating-like redistribution of scattered light with useful angle selective properties as described below. Such redistribution can be achieved by a nominally repeating structure (which may or may not be well spatially correlated over any significant distance), which simply has the property of preferential light redistribution.

The present invention teaches a method for observing, and if necessary enhancing, the contrast of a grain defect or defects. The process of the present invention can be performed manually or in combination with an automated apparatus. A preferable application of the present invention consists of using light comprised predominantly of visual spectrum wavelengths although wavelengths outside the visual range can be used under certain conditions as described more fully below.

Figure 1:
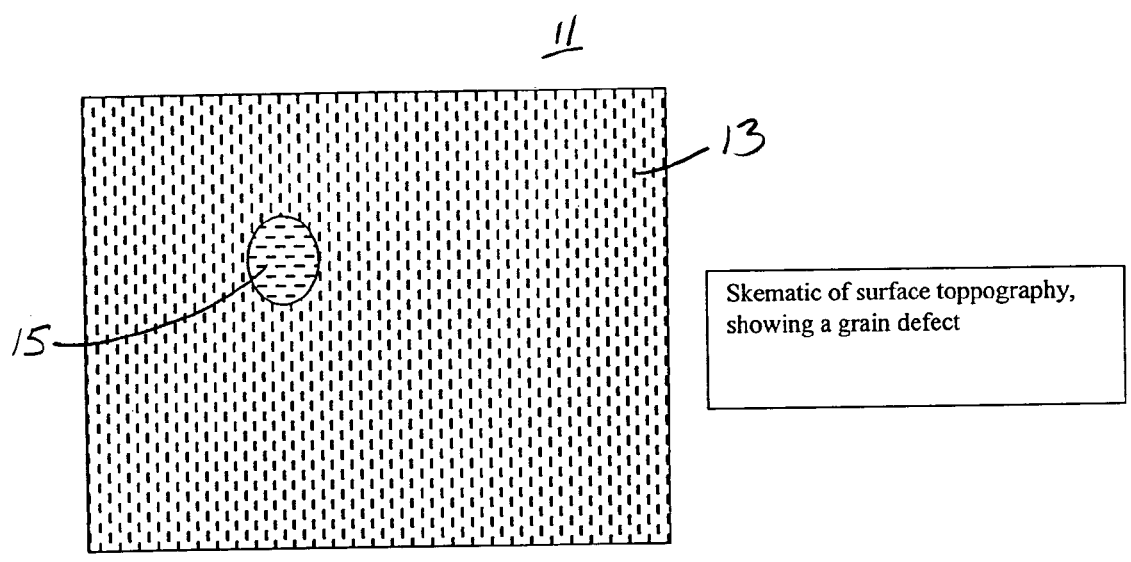
FIG. 1 A schematic diagram of the surface topography of a metallic part containing a grain defect.

With reference to FIG. 1, there is illustrated a schematic diagram of the surface topography of a metallic surface 11 comprised, in part, of a surface defect 15 (a defect which intersects the surface). Surface defect 15 illustrates the contrast between the surface grain defect 15 and that of the surrounding inherent surface grain 13. As used herein, "repeating microstructure" refers to a small scale physical structure present on a metallic surface which repeats in a nominally continuous and discernable manner over the extent of the surface but which may or may not be phase correlated over any range within the grain.

Note that microstructure is the regular repeating array. The present invention makes use of the regular array as an ensemble in the inspection. The regular array in the surface grain defect 15 is oriented differently than the regular array in the surrounding grain. (For each grain, the regular array is oriented differently.) The present invention makes use of this regular array to produce the enhanced contrast.

For example, a grating-like effect is enabled by a cuboidal volume array comprising 300 nm gamma prime precipitate in a nickel based superalloy or by a laminar array such as induced in IN939 or gamma TiAl to create the light scatter manipulated to produce the enhanced contrast. In the specific case of a directional solidified Ni alloy casting, for example, the range of grain defects normally observed are ~0.001 inch and larger. Note that an example would be a so called freckle grain which has different geometric scattering characteristics than those of the surrounding grain.

Note that two characteristic dimensions are involved. One is the minimum surface grain size (S) that can be observed by a particular measurement technique of interest. The other is the spacing (d) between the nominally regular array observed on the surface.

The preferred method is to prepare the article for inspection to optimize the diffraction environment then inspect the article using an appropriate observation protocol.

In a preferred embodiment, the minimum detectable grain size (S) is typically no smaller than the wavelength of light used to illuminate the surface. In the case of visible light, this dimension is on the order of half of a micrometer. In practice, the minimum that is most preferred, for a directionally cast Ni based superalloy, is close to 0.001". Note that this distance is not the grating spacing (d) of the diffraction grating. The grating spacing (d) is typically a function of the inherent spacing between the volume elements leading to the formation of the repeating features and the section angle cut thru the features.

As illustrated, the grating geometry of surface defect 15 is shown oriented in a direction different from that of surface grain 13. Note that alternatively it may have a different grating spacing or a combination of the two.

Note that a common method of generating such surfaces is etching (which involves the corrosive action of an etchant). Additional methods of creating a surface topography exist (which are known to those familiar with the art).

Depending upon their size and transparency to incident light, surface and volume, structures which exhibit repetitive surface patterns may diffract light into non-random geometries that are detectable. Likewise, interruptions to such repetitive surface patterns, such as those caused by defects, are similarly detectable by their contrast. It is a central insight of the present invention that the presence of a surface defect 15 imbedded within a surrounding surface grain 13 may be visually detected by redirecting a light beam of an appropriate wavelength off of the surface defect 15 and the surrounding surface grain 13 and observing the difference between the light scattering properties of each. The spectrum of the light beam is chosen to provide a contrast between the light redirected from the surface defect 15 and the surface grain 13 sufficient to permit visual differentiation.

The light scattering properties of a material can be described by the bidirectional reflectance distribution function (BRDF). In practice, the BRDF characteristics of a surface are determined by measuring the intensity of scattered light at various angles for various incident beam angles. While a "complete" BRDF would require extensive measurements of scattered light at all scatter angles for all incident angles with all polarization states and at all wavelengths, practical measurements encompass a somewhat smaller variable space with quite acceptable results. For example, many "well behaved" surfaces can be adequately understood throughout their full 2 pi steradian reflection space (or 4 pi for objects with transmission) with measurements taken exclusively within a two dimension slice of a plane defined by the incident and specular beams.

In accordance with the present invention, metallic surface 11 is comprised of a surface grain 13 that exhibits repetitive features which interact with light in a periodic manner. This interaction has ramifications for the surface grain 13 BRDF as the surface grain 13 functions, in part, like a diffraction grating. Diffraction gratings embody equally spaced lines which modify the phase front of the light in such a manner that a portion of the redirected light reconstructs to form one or more additional beams of light emanating from the surface in one or more directions other than that of the specular beam.

Figure 4:
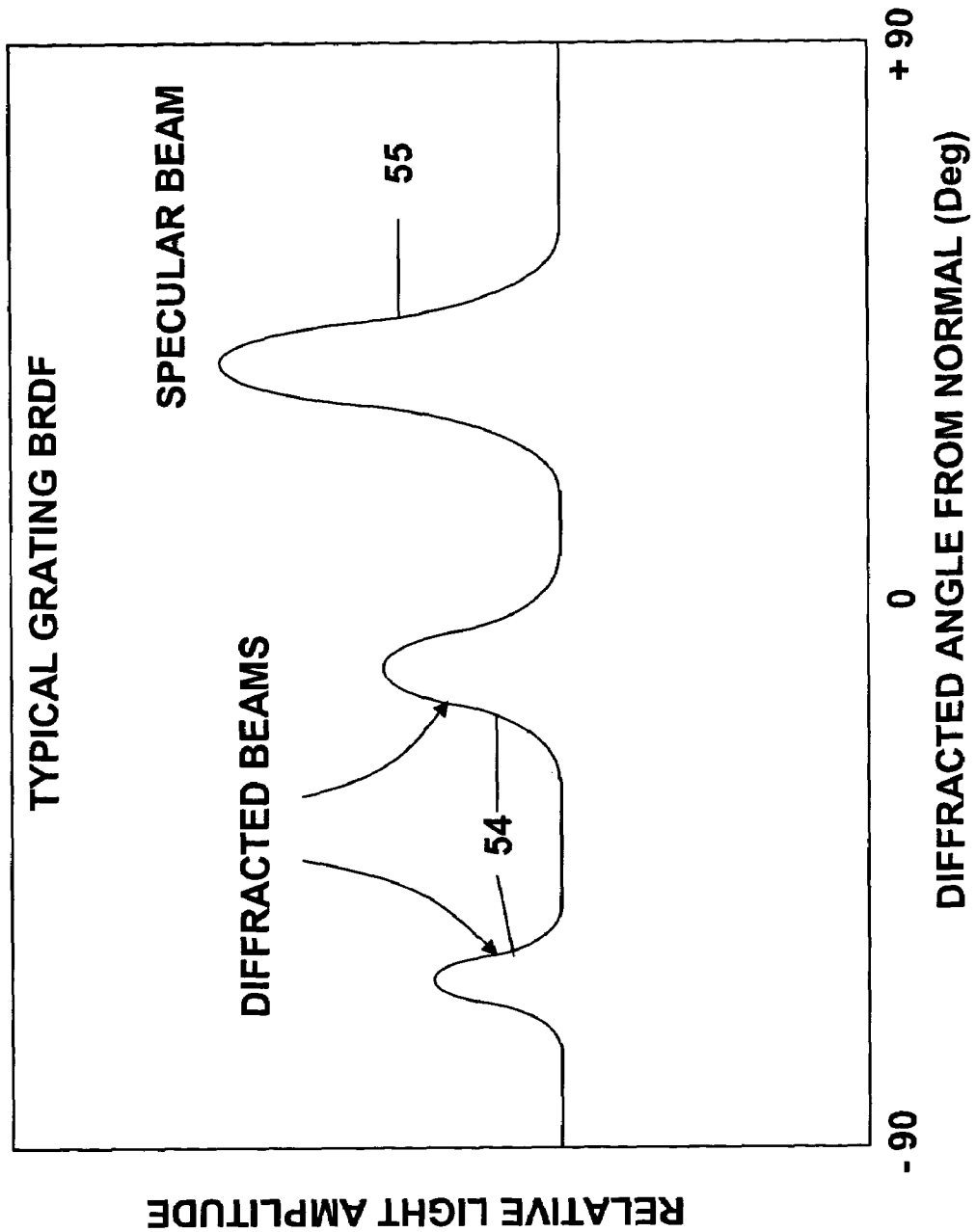
FIG. 4 A 2D bidirectional reflectance distribution function (BRDF) plot of a surface of the present invention.

An example of such a 2D BRDF plot is shown in FIG. 4. It shows the amplitude of the scattered light energy as a function of scattered angle which is often defined with the normal to the surface as being 0 degrees with radiation scattered along the surface back toward along the projection of the incident beam as −90 deg while that which grazes the surface along the specular beam projection is at +90 deg from the normal. This system can be defined with an angular range of 0–180 deg, or by the use of direction cosines or any other convenient angular space convention.

Diffraction gratings are well known optical devices which can redirect incident light into selected preferential directions depending upon the incident beam geometry, repetitive spacing of the grating and the wavelength(s) of interest. Real surfaces, which are imperfectly polished or which may have a random topology either or both in amplitude and feature spacing, usually contain the equivalent of many such gratings of different geometries, which tend to redirect incident light in substantially random directions. The imposition of one or more of such gratings with greater redirective power than the relatively inefficient "random" gratings of the embedded scratches (the "optical noise"), generates a preferentially detectable signal at one or more preferred angles. This is exemplified by blazed gratings and the Littrow grating, which have long been used for astronomical spectroscopy, by which narrow selected wavelength bands of starlight are redirected into a very narrow angle with very high efficiency.

Figure 5:
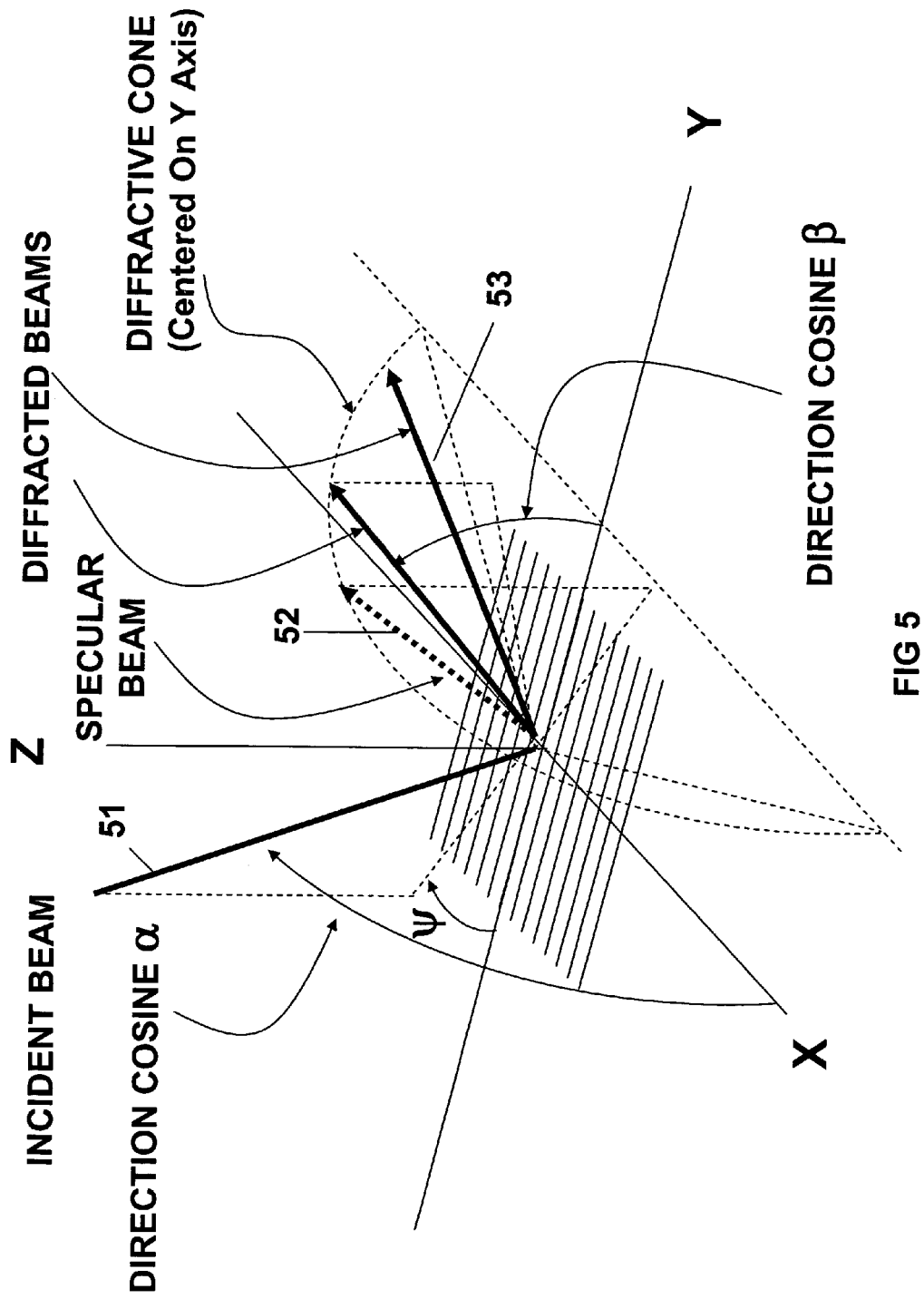
FIG. 5 An illustration of a typical diffraction grating beam redirection geometry.

The redirective geometry of a reflection grating is given by the equations $$\alpha_{inc}+\alpha_n=n\lambda/d \qquad 1.$$

$$\beta_{inc}+\beta_n=0 \qquad 2.$$

Where $\alpha$ and $\beta$ are the direction cosines of the incident, specular (n=0) and diffracted (n<>0) orders of a narrow band collimated beam of light, and where the continuous features of the grating are parallel with the x axis. The geometry is shown in FIG. 5.

As noted above, such regularly spaced features can be generated in metallic surfaces by the etching of grains with repeating structures or by the naturally occurring crystallographic orientations present in a finished part which exhibit distinctive light reflective or redirected properties such as a different index of refraction or a different level of light absorption with respect to grain defects 15.

The operant benefit of the subject invention is the improved viewability that is obtained by the use of specially configured light (or electromagnetic radiation) in combination with the special characteristics of the features being investigated; eg the features exhibit some of the properties of one or more diffraction gratings. In some cases, the crossed grating characteristics of a rectangular feature array can also be used to advantage. Such crossed grating features can be seen in polished superalloys with different embedded material phases (such as gamma & gamma prime).

Note however, that that the grating equation requires that, for real grating diffracted orders to exist, the conditions of equation must be met. Thus, for sufficiently large ratios of $n\lambda/d$, no diffraction grating beams are generated.

An example of this improved signal to noise (S/N) is exemplified in diffraction order "bumps" noted earlier in FIG. 4. In this case, to ease visualization, it is assumed that the diffraction grating lines are oriented perpendicular to the incident beam path (where y=90 degree in FIG. 5). This constrains the specular and diffracted beams to the plane defined by the incident 51 & specular 52 beams. The presence of the specular 55 and diffracted beam 54, at increased signal levels above the general broadband background scatter (FIG. 4.) is indicated by the diffractive peaks at the diffraction angles defined by the equations above.

In one embodiment, illumination by a source comprising one or a small number of narrow wavelength bands is employed to provide especially high S/N performance. Since, per equation 1, the diffracted angle depends on the incident wavelength (with the grating order and line spacing constant), a broader range of wavelengths will tend to spread over a greater angular range. This tends to reduce the amplitude of the diffraction peak (for beam of fixed light energy) and thus reduces the S/N. The narrow band mode of operation can be achieved by using a narrow band light source such as a laser or by the use of filtered light (either at the source or between the diffraction surface and the sensor or observer), with a wavelength relatively close to (but much larger than) the grating spacing (d). Under this condition, higher orders (n=1, n=−1, n=2, etc) are well separated and provide clear discrimination from the surround which exhibits little or no grating effect.

However, it must be noted, as a second embodiment, that narrow band filtering may not be needed in all cases as long as an acceptable S/N is achieved. For example, a small aperture white light source, such as a standard incandescent lamp, is quite effective in the visual screening of a surface to identify local grating-like regions. This is particularly effective when the grating line spacing (d) is comparable to or somewhat larger than the magnitude of the typical wavelength used. For example, visible light, which is in the 0.4–0.7 micrometer range, is quite effective in observing periodic features with line spacings of the same dimensions, in the (non-exclusive) case of a viewing angle along the surface normal and with illumination at high angles from the normal.

The above concepts apply to reflective and transmissive gratings as well as volume coherent structures such as Bragg gratings.

While the effectiveness in discriminating adjacent wavelengths improves with the surface size and coherence of the grating, relatively "poor" gratings can achieve substantial angular and S/N discrimination between wavelength bands. This is one of the features which enable the subject invention.

Figure 2:
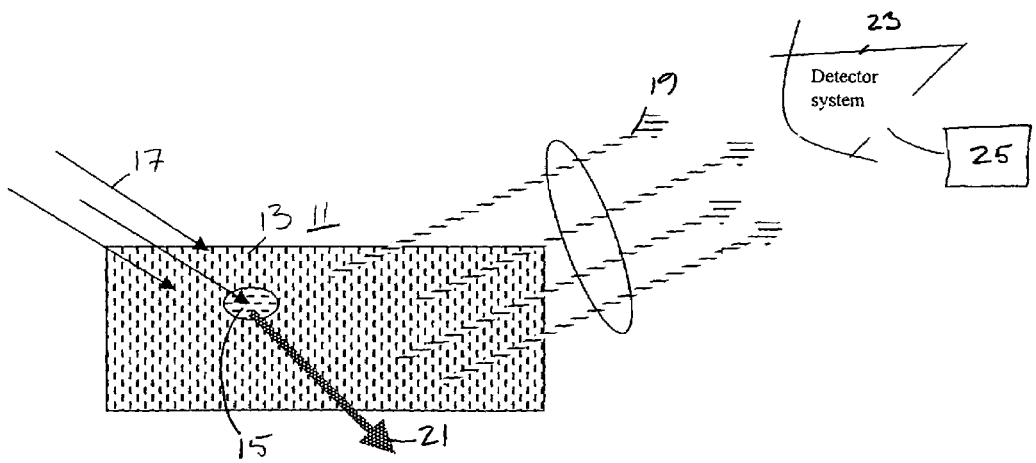
FIG. 2 A diagram of the grain inspection apparatus of the present invention.

With reference to FIG. 2, there is illustrated the manner in which grain defects are detected by the present invention. Light beam 17 of a wavelength and incident geometry selected as described above redirects off of surface grain 13 and surface defect 15. A portion of light beams 17 redirected off of surface grain 13 non-specularly propagate preferentially toward the detector system 23 so as to be detected by detector system 23 as redirected light 19. The portion of light beam 17 redirected off of surface defect 15 is shown as redirected defect light 21. Only a small portion of the light redirected from any location within the defect, wherein said light is predominantly Lambertian scatter, contributes to light beam 19 which is collected by detector system 23, as compared to the magnitude of light collected from a comparably sized location in the grain outside of the defect. While redirected light 19 propagates towards detector system 23, redirected defect light 21 is largely redirected away from detector system 23. Detector system 23 may be any system or apparatus capable of perceiving, recording or otherwise discerning light. In a preferred embodiment, detector system 23 consists of a photographic medium such as film, or a CCD. In another embodiment, detector system 23 consists of an observer's eye. Obviously, the absolute and relative (either can be larger) sizes of the grain defect and surrounding grain are limited only by the spatial resolution of the detector system.

Figure 3:
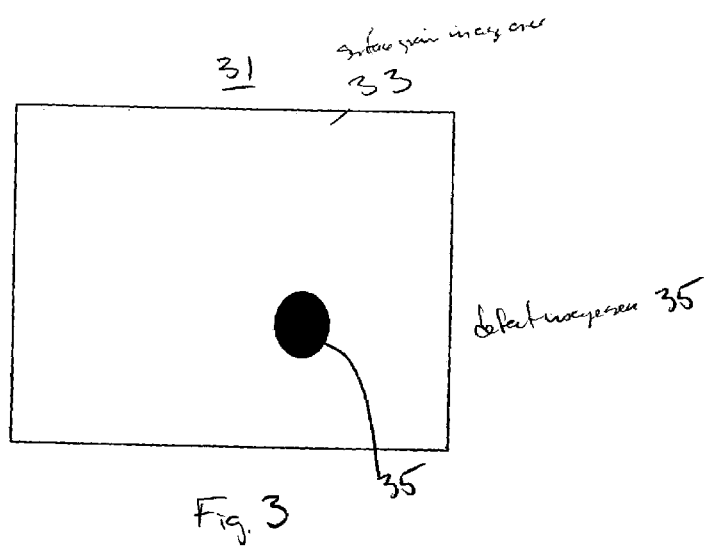
FIG. 3 An illustration of a grain detection image of the present invention.

With respect to FIG. 3, there is illustrated image 31 created by or perceived by detector system 23. As is evident, there is substantial visual contrast between the part of the image comprised of values associated with redirected light 19, namely surface grain image area 33, and defect image area 35 corresponding to the area comprised of surface defect 15. As is evident, surface grain image area 33 and defect image 35 exhibit different visual characteristics. In a preferred embodiment, detector system 23 employs image processing mechanism 25 to perform automated image processing upon image 31. Image processing mechanism 25 preferably employs a technique including but not limited to edge detection to discern the boundaries of defect image area 35. In this manner, detector system 23 can identify defect image area 35 corresponding to a surface defect 15 of metallic surface 11.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A method for detecting an existence of a surface defect in a metallic part comprising the steps of:
   providing a metallic part having a normal grain structure for examination;
   visually determining if there is a defect in a surface of said metallic part, which surface defect has a grain structure oriented differently than the normal grain structure; and
   said visual defect determining step comprising, generating a light beam of appropriate wavelength, redirecting the light beam of appropriate wavelength off of a surface of said metallic part and determining the existence of any difference between a first light scattering property created by the differently oriented grain structure in the surface defect and a second light scattering property created by a surrounding normal grain structure.

2. The method according to claim 1, wherein said light beam redirecting step comprises providing a light beam having a spectrum for providing a contrast between light redirected from the surface defect and the surrounding normal grain structure sufficient to permit visual differentiation.

3. The method according to claim 1, wherein said metallic part providing step comprises providing a metallic part having a surface comprised of a normal surface grain that exhibits repetitive features which interact with light in a periodic manner.

4. The method according to claim 1, wherein said existence determining step comprises providing a detecting system and using said detecting system to detect a portion of said light beam redirected off said normal grain structure.

5. The method according to claim 4, wherein said detecting system providing step comprises providing a detecting system which utilizes film.

6. The method according to claim 4, wherein said detecting system providing step comprises providing a CCD detection system.

7. The method according to claim 4, wherein said detecting system providing step comprises providing a detector system which employs image processing mechanism to perform automated image processing upon an image of the surface of the metallic part.

8. The method according to claim 7, wherein said difference existence determining step further comprises using said image processing mechanism to discern boundaries of any defect image area corresponding to the surface defect.

9. The method according to claim 1, wherein said light beam generating step comprises generating said light beam using a laser.

10. The method according to claim 1, wherein said light beam generating step comprises generating a filtered light beam where a filter is used at a source.

11. The method according to claim 1, wherein said light beam generating step comprises generating a filtered light beam with a filter located between a diffraction surface and one of a sensor and an observer.

12. The method according to claim 1, wherein said light beam generating step comprises generating a light beam having a wavelength not greater than twice a regular array spacing.

13. The method according to claim 1, wherein said light beam generating step comprises generating a light beam having a wavelength band between 0.4 to 0.7 micrometers.

14. The method according to claim 1, wherein said metallic part providing step comprises providing a turbine engine component.

15. A system for detecting an existence of a surface defect in a metallic turbine engine part having a normal grain structure, said system comprising:
   means for visually determining if there is a defect in a surface of said metallic turbine engine part, which surface defect has a grain structure oriented differently than the normal grain structure; and
   said visual defect determining means comprising means for generating a light beam of appropriate wavelength and for redirecting the light beam of appropriate wavelength off of a surface of said metallic turbine engine part and means for determining the existence of any difference between a first light scattering property created by the differently oriented grain structure in the surface defect and a second light scattering property created by a surrounding normal grain structure.

16. The system according to claim 15, wherein said light beam generating and redirecting means comprises means for providing a light beam having a spectrum for providing a contrast between light redirected from the surface defect and the surrounding normal grain structure sufficient to permit visual differentiation.

17. The system according to claim 15, wherein said existence determining means comprises a detecting system for detecting a portion of said light beam redirected off said normal grain structure.

18. The system according to claim 17, wherein said detecting system comprises a detecting system which utilizes film.

19. The system according to claim 17, wherein said detecting system comprises a CCD detection system.

20. The system according to claim 17, wherein said detecting system comprises a detector system which employs image processing mechanism to perform automated image processing upon an image of the surface of the metallic turbine engine part.

21. The system according to claim 20, further comprising said image processing mechanism including means to discern boundaries of any defect image area corresponding to the surface defect.

22. The system according to claim 15, wherein said light beam generating means comprises a laser.

23. The system according to claim 15, wherein said light beam generating means comprises means for generating a filtered light beam where a filter is used at a source.

24. The system according to claim 15, wherein said light beam generating means comprises means for generating a filtered light beam with a filter located between a diffraction surface and one of a sensor and an observer.

25. The system according to claim 15, wherein said light beam generating means comprises means for generating a light beam having a wavelength not greater than twice a regular array spacing.

26. The system according to claim 15, wherein said light beam generating means comprises means for generating a light beam having a wavelength band between 0.4 to 0.7 micrometers.

* * * * *